(12) United States Patent
Artico et al.

(10) Patent No.: US 8,455,678 B2
(45) Date of Patent: Jun. 4, 2013

(54) PROCESS FOR THE PREPARATION OF FESOTERODINE WITH LOW IMPURITIES CONTENT

(75) Inventors: Marco Artico, Parabiago (IT); Emanuele Attolino, Palagiano (IT); Pietro Allegrini, San Donato Milanese (IT)

(73) Assignee: Dipharma Francis s.r.l., Baranzate (IT)

( * ) Notice: Subject to any disclaimer, the term of this patent is extended or adjusted under 35 U.S.C. 154(b) by 142 days.

(21) Appl. No.: 12/972,573

(22) Filed: Dec. 20, 2010

(65) Prior Publication Data
US 2011/0152367 A1    Jun. 23, 2011

(30) Foreign Application Priority Data
Dec. 21, 2009   (IT) .............................. MI2009A2255

(51) Int. Cl.
*C07C 67/28*   (2006.01)
(52) U.S. Cl.
USPC ......................................................... 560/252
(58) Field of Classification Search
None
See application file for complete search history.

(56) References Cited

U.S. PATENT DOCUMENTS

| | | |
|---|---|---|
| 6,713,464 B1 | 3/2004 | Meese et al. |
| 6,858,650 B1 | 2/2005 | Meese et al. |
| 2011/0171274 A1* | 7/2011 | Neela et al. .................. 424/400 |

FOREIGN PATENT DOCUMENTS

| | | |
|---|---|---|
| EP | 1927585 A2 | 4/2008 |
| EP | 2281801 A1 | 9/2011 |
| WO | 2007140986 A1 | 12/2007 |
| WO | 2010/010464 A2 | 1/2010 |

OTHER PUBLICATIONS

Mohan et al, Journal of Pharmaceutical and Biomedical Analysis, Identification and Characterization of a Principal Oxidation Impurity in Clopidogrel Drug Substance and Drug Product, 2008, 47, pp. 183-189.*

Reddy et al, Journal of Pharmaceutical and Biomedical Analysis, Structural Identification and Characterization of Potential Impurities of Pantoprazole Sodium, 2007, 45, pp. 201-210.*

U.S. Appl. No. 13/295,224, filed Nov. 14, 2011 in the name of Marco ARTICO entitled: "Process for the Preparation of Fesoterodine or a Salt Thereof.".

* cited by examiner

*Primary Examiner* — Paul A Zucker
(74) *Attorney, Agent, or Firm* — Rothwell, Figg, Ernst & Manbeck, P.C.

(57) ABSTRACT

Disclosed is a process for the preparation of (R)-2-(3-diisopropylamino-1-phenylpropyl)-4-(hydroxymethyl)-phenol isobutyrate (Fesoterodine) or a pharmaceutically acceptable salt thereof having a low content of impurities such as tolterodine and tolterodine isobutyrate.

15 Claims, No Drawings

PROCESS FOR THE PREPARATION OF FESOTERODINE WITH LOW IMPURITIES CONTENT

FIELD OF INVENTION

The present invention relates to a process for the preparation of (R)-2-(3-diisopropylamino-1-phenylpropyl)-4-(hydroxymethyl)-phenol isobutyrate (Fesoterodine), or a pharmaceutically acceptable salt thereof, having a low impurity content, including the impurities tolterodine and tolterodine isobutyrate.

PRIOR ART

Many attempts have been made over the years to prepare pharmaceutical products containing very low amounts of impurities. Impurity control is a key parameter when evaluating the efficiency of a process, and requires the study of an enormous number of options to decide on the reaction conditions and control protocols needed to ensure that medicaments administered to the public are pure, and consequently safer.

The guidelines established by regulatory bodies such as the US Food and Drug Administration (FDA) suggest that the impurities in medicaments should be identified if present in excess of 0.1% (namely 1,000 ppm). "ppm" means parts per million, so 1% corresponds to 10,000 ppm; 0.1% corresponds to 1,000 ppm; 0.01% corresponds to 100 ppm, and 0.001% corresponds to 10 ppm.

Fesoterodine, or (R)-2-(3-diisopropylamino-1-phenylpropyl)-4-(hydroxymethyl)-phenol isobutyrate, of formula (I)

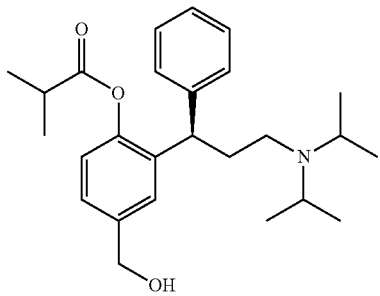

(I)

is a known compound with antimuscarinic activity, used in clinical practice in the form of fumarate salt to treat overactive bladder syndrome, and in particular, urinary incontinence.

U.S. Pat. No. 6,713,464 describes its preparation by various synthesis methods, one of which is the scheme shown below.

Scheme

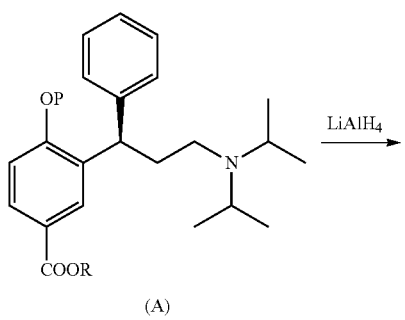

(A)

LiAlH₄ →

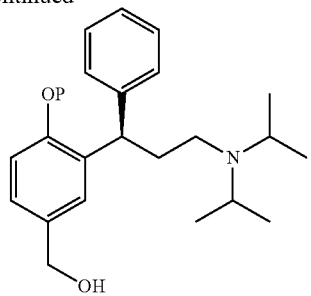

(B)

P = protective group
R = H, alkyl

Some of these methods use as key intermediate a compound of formula (A), where R is a hydrogen or a methyl and the P protecting group of the phenolic hydroxyl group, when present, is normally benzyl. Reduction of the carboxyl function with LiAlH₄ leads to the compound of formula (B), either protected or unprotected on the phenolic hydroxyl group which, after optional deprotection and selective esterification, leads to Fesoterodine of formula (I).

It has been demonstrated that the compounds of formula (VIII) (tolterodine) and (IX) (tolterodine isobutyrate) are typical impurities of Fesoterodine when prepared by this synthesis method.

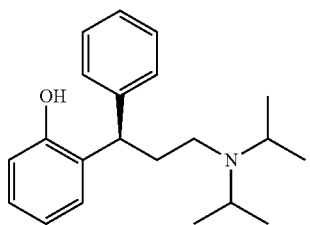

(VIII)

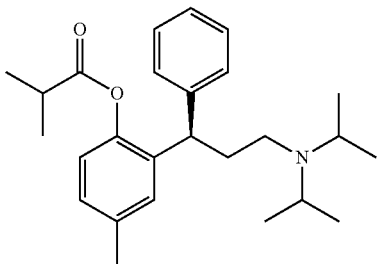

(IX)

The formation of the compound of formula (VIII) during the reduction reaction of a compound of formula (A) as described above with lithium aluminium hydride is probably due to the fact that the reaction is not very chemoselective. For example, in some cases the conversion of a methylester of formula (A), deprotected at the phenolic hydroxyl group, to the corresponding derivative of formula (B), by reduction reaction with lithium aluminium hydride at 25° C. in tetrahydrofuran, in agreement with U.S. Pat. No. 6,713,464, produces, as the main product, the compound of formula (VIII). An alternative reduction method, which supplies Fesoterodine, or a pharmaceutically acceptable salt thereof, with a low impurity content, such as tolterodine of formula (VIII) and/or tolterodine isobutyrate of formula (IX), is therefore needed.

SUMMARY OF THE INVENTION

A process has now been found, which overcomes the problems reported above and produces Fesoterodine, or a pharmaceutically acceptable salt thereof, having a low impurity content.

DETAILED DISCLOSURE OF THE INVENTION

Object of the invention is a process for the preparation of a compound of formula (I), or a salt thereof,

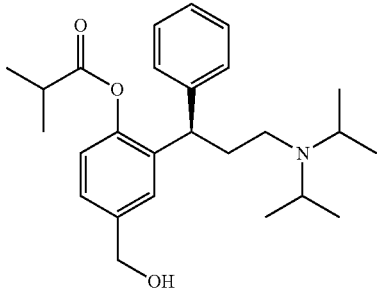

(I)

containing an amount of a compound of formula (VIII)

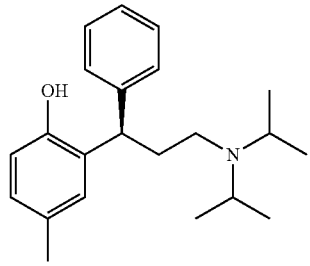

(VIII)

equal to or lower than 0.05% and typically equal to or higher than about 0.0001% and/or an amount of a compound of formula (IX)

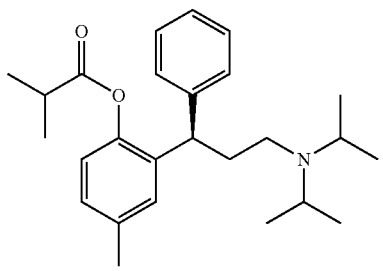

(IX)

equal to or lower than about 0.1% and typically equal to or higher than about 0.0001%, comprising:

the chemoselective reduction of the carboxylate group of a compound of formula (IIa)

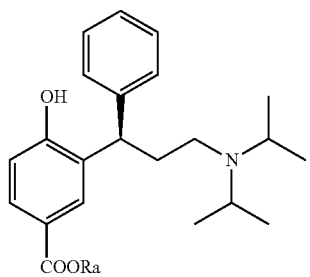

(IIa)

wherein Ra is a $C_1$-$C_6$ alkyl, to obtain a compound of formula (III),

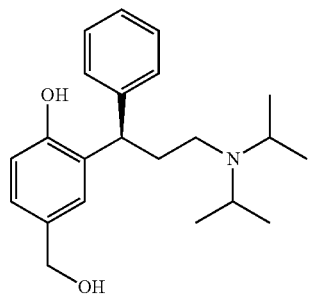

(III)

and the subsequent selective esterification of the phenolic hydroxy group of the resulting compound of formula (III) to obtain a compound of (I), and, if desired, the conversion of a compound of formula (I) into a salt thereof;
wherein the chemoselective reduction comprises:
a) the treatment of a compound of formula (IIa), as defined above, with sodium or potassium hydroxide in an organic solvent to obtain a phenate intermediate of formula (X)

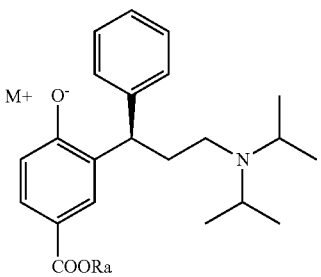

(X)

wherein Ra is as defined above; and $M^+$ is $Na^+$ or $K^+$; and
b) the subsequent reduction with lithium aluminium hydride in an organic solvent.

A $C_1$-$C_6$ alkyl group, which may be straight or branched, is typically a $C_1$-$C_4$ alkyl group, for example methyl, ethyl or isopropyl, preferably a methyl group.

The amount of sodium hydroxide or potassium hydroxide used is typically stoichiometric to the compound of formula (IIa).

The reaction of a compound of formula (IIa) with sodium hydroxide or potassium hydroxide can be carried out for example in a solvent selected from a $C_3$-$C_8$ ketone, preferably acetone or methyl ethyl ketone; a cyclic or acyclic ether, typically tetrahydrofuran; an ester, typically ethyl acetate; a straight or branched $C_1$-$C_6$ alkanol, preferably a $C_1$-$C_4$ alkanol, typically methanol.

The resulting phenate intermediate of formula (X) can be used as such or isolated, for example by evaporating the reaction solvent under reduced pressure. The thus isolated compound can be used as such, without further purification.

The reduction reaction of the phenate intermediate of formula (X) can be carried out in a temperature range from about 0° C. to the reflux temperature of the reaction mixture. Temperature preferably ranges from about 0° C. to about 10° C.

The reaction is typically carried out in the presence of a cyclic or acyclic ether, such as diethyl ether, dioxane, tetrahydrofuran, preferably tetrahydrofuran.

The amount of lithium aluminium hydride used is at least stoichiometric to the compound of formula (X) and preferably ranges between about 1 and 5 mols per mols of a compound of formula (X), more preferably between about 1 and 3 mols.

The selective esterification reaction of a compound of formula (III) can be carried out according to known procedures, for example according to U.S. Pat. No. 6,713,464.

A salt of a compound of formula (I) is preferably a pharmaceutically acceptable salt thereof, for example the fumarate, citrate, hydrochloride or sulfate salt, preferably the fumarate or sulfate salt.

The conversion of a compound of formula (I) to a salt thereof can be carried out according to known procedures.

Furthermore, a salt of a compound of formula (I) can be converted into the free base according to known procedures.

A compound of formula (IIa) can be obtained by a process comprising the resolution of the corresponding racemate of formula (II)

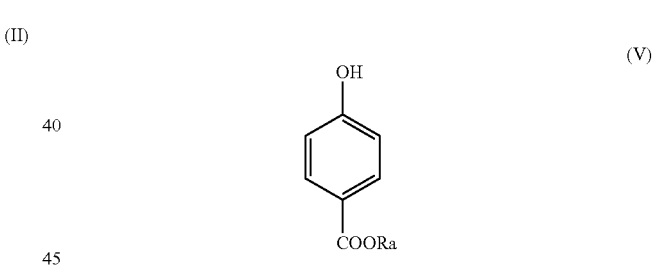

(II)

wherein Ra is as defined above, through formation of a diastereomeric salt thereof with an optically active organic acid.

An optically active organic acid can be an optically active carboxylic or sulfonic acid.

An optically active carboxylic acid can be selected for example from (+) or (−) tartaric acid, (+) or (−) 2,3-dibenzoyl-tartaric acid, mandelic acid, 3-chloro-mandelic acid and abietic acid; an optically active sulfonic acid is for example S-(+)-camphorsulfonic acid.

The reaction for the resolution of the diastereomeric salt can be carried out in a solvent, selected for example from water, a dipolar aprotic solvent, typically dimethylformamide, dimethylacetamide, acetonitrile, dimethylsulfoxide; a $C_3$-$C_8$ ketone, for example acetone, methyl ethyl ketone, methyl isobutyl ketone; a cyclic or acyclic ether, typically tetrahydrofuran, dioxane or methyl-tert-butyl ether; an ester, typically ethyl acetate, isopropyl acetate, butyl acetate; a chlorinated solvent, typically dichloromethane; a polar protic solvent such as a straight or branched $C_1$-$C_6$ alkanol, for example a $C_1$-$C_4$ alkanol, typically methanol, ethanol, isopropanol or butanol; or a mixture of two or more, typically two, of said solvents. The resolution reaction can be preferably carried out in a $C_1$-$C_6$ alkanol, for example a $C_1$-$C_4$ alkanol, typically methanol, ethanol, isopropanol or butanol.

The diastereomeric salt of a compound (IIa) can be separated from the salt of its isomer (IIb)

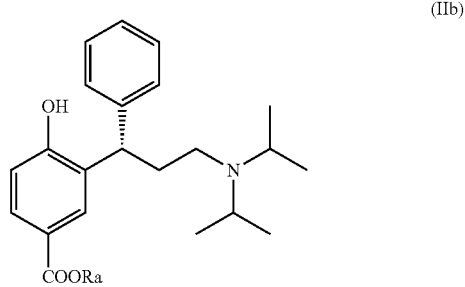

(IIb)

wherein Ra is as defined above, for example by crystallization from the reaction mixture, recovered and then cleaved to obtain the respective compound (IIa). The separation, recovery and cleavage of the salt can be carried out according to known techniques.

A compound (IIa) has high enantiomeric purity. The enantiomeric purity of an enantiomer (IIa), calculated by chiral HPLC, expressed in terms of enantiomeric ratio, is typically equal to or higher than 95:5, preferably equal to or higher than 99:1.

A compound of formula (II), or a salt thereof, can be prepared for example by a process comprising the reaction of a compound of formula (V)

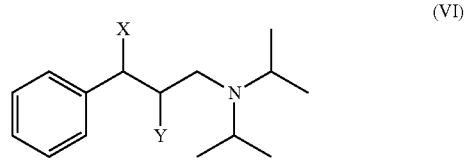

(V)

wherein Ra is as defined above, with a compound of formula (VI)

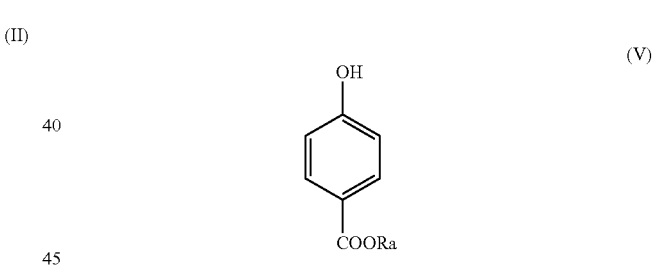

(VI)

wherein X is a group capable of generating a benzyl carbocation and Y is hydrogen, or X and Y, taken together, form a double bond; in the presence of a strong acid.

X as a group capable of generating a benzyl carbocation is for example a hydroxy group or a reactive derivative thereof, such as a $C_1$-$C_6$ alkyl ether or aryl ether, a $C_1$-$C_6$ alkylcarboxylate or aryl carboxylate, a $C_1$-$C_6$ alkylsulfonate or aryl sulfonate, a trifluoromethanesulfonate, a sulfate, nitrate or phosphate; or a halogen, for example chlorine, bromine or iodine.

A strong acid, as herein defined, can be a strong protic acid or a Lewis acid, wherein a strong protic acid is selected for example from hydrochloric, sulfuric, hydrobromic, perchloric, polyphosphoric, trifluoroacetic, methanesulfonic, p-toluenesulfonic and trifluoromethanesulfonic acids, preferably methanesulfonic acid; a Lewis acid can be selected from $AlCl_3$, $FeCl_3$ and $BF_3$ etherate.

When X is a hydroxy group or a $C_1$-$C_6$ alkylether or aryl ether and Y is hydrogen, or when X and Y, taken together, form a double bond, the strong acid is preferably protic; whereas when X is a halogen atom and Y is hydrogen, the strong acid is preferably a Lewis acid.

By proceeding analogously to the process of the present invention for preparing a compound of formula (I), starting from a compound of formula (IIb), the (S) enantiomer of a compound of formula (I), i.e. (S) Fesoterodine or a salt thereof, containing an amount of the (S) enantiomer of a compound of formula (VIII) equal to or lower than 0.05% and typically equal to or higher than about 0.0001% and/or an amount of the (S) enantiomer of compound of formula (IX) equal to or lower than about 0.1% and typically equal to or higher than about 0.0001% can be obtained.

A compound of formula (IX), as defined above, can be prepared from tolterodine of formula (VIII), as reported above, for example by esterification of the phenol hydroxyl with isobutyryl chloride according to known procedures.

The process of the invention provides Fesoterodine of formula (I) or a pharmaceutically acceptable salt thereof, as defined above, containing an amount of a compound of formula (VIII) typically equal to or lower than about 0.05% and typically equal to or higher than about 0.0001% and/or an amount of a compound of formula (IX) typically lower than or equal to about 0.1% and typically equal to or higher than about 0.0001%.

Therefore, an object of the present invention is also a mixture comprising a compound of formula (I), or a pharmaceutically acceptable salt thereof, as defined above, and a compound of formula (VIII) in an amount typically equal to or lower than about 0.05% and typically equal to or higher than about 0.0001%, and/or an amount of a compound of formula (IX) typically lower than or equal to about 0.1% and typically equal to or higher than about 0.0001%.

A further object of the present invention is a pharmaceutical composition comprising a compound of formula (I), or a pharmaceutically acceptable salt thereof, as defined above, and a compound of formula (VIII) in an amount typically equal to or lower than about 0.05% and typically equal to or higher than about 0.0001%, and/or an amount of a compound of formula (IX) typically lower than or equal to about 0.1% and typically equal to or higher than about 0.0001%, and a pharmaceutically acceptable excipient and/or carrier.

The pharmaceutical composition of the invention can be prepared according to methods known in the pharmaceutical technique, in different pharmaceutical forms, such as tablets, powders, lozenges, capsules, syrups, injectable solutions and controlled release pharmaceutical formulations. Examples of excipients can be ligands, disintegrants, diluents, suspending agents, emulsifiers and flavours. The dosage for the administration to a mammal, including humans, is typically the same as that used clinically for Fesoterodine. Anyway, the choice of the dosage is left to physician's discretion.

The amount of each impurity of formula (VIII) or (IX), as defined above, in a mixture comprising a compound of formula (I), and one or both said impurities of formula (VIII) and formula (IX), can be determined according to the usual analytic techniques. By way of example, impurities of formula (VIII) and (IX) can be detected by normal or reversed phase HPLC.

The evaluation of the content in impurities of formula (VIII) and (IX) is crucial, particularly in a process for the preparation of Fesoterodine or a pharmaceutically acceptable salt thereof, as it affects the industrial applicability of the process itself.

In particular, a compound of formula (VIII) and/or a compound of formula (IX) can be used as an analytical standard. Therefore, a further object of the present invention is the use of a compound of formula (VIII) and of formula (IX), as defined above, as an analytical standard in a process for the preparation of Fesoterodine of formula (I), or a pharmaceutically acceptable salt thereof, as defined above.

Therefore, a further object of the present invention is a process for the preparation of Fesoterodine of formula (I), or of a pharmaceutically acceptable salt thereof, as defined above, comprising the use of a compound of formula (VIII) and/or (IX), as an analytical standard.

The following examples illustrate the invention.

Example 1

Synthesis of R-(+)-2-(3-Diisopropylamino-1-phenyl-propyl)-4-hydroxymethyl-phenol (Compound of Formula III)

Methyl R-(−)-3-(3-diisopropylamino-1-phenyl-propyl)-4-hydroxy-benzoate (IIa) (13.5 g, 36.5 mmols) is dissolved in methanol (100 ml) in a round-bottom flask under inert atmosphere and the solution is cooled to 0-5° C. A 5% NaOH solution in methanol (29.2 g, 36.5 mmols) is slowly dropped therein, then the bath is brought to a temperature of 35° C. and methanol is distilled off under reduced pressure. The obtained residue is dissolved in tetrahydrofuran (65 ml) and the resulting solution is slowly dropped (about 1 hour) into a suspension of lithium aluminium hydride (2.8 g, 73 mmols) in tetrahydrofuran (28 ml), monitoring for the mixture temperature not to exceed 5° C. Stirring is continued at the same temperature for two hours, then the mixture is slowly brought to about 25° C. HPLC monitoring of the reaction evidences after 1 hour the complete disappearance of (IIa) and the presence of less than 0.10% of (VIII). The mixture is cooled to 0-5° C., diluted with tetrahydrofuran (60 ml) and added in succession with $H_2O$ (2.8 ml), 15% NaOH (8.4 ml), $H_2O$ (2.8 ml) and the suspension is left under stirring for 3 hours. The obtained salts are filtered off and the organic solution is concentrated under reduced pressure to yield 12.4 g of (III) in a yield higher than 98% and a content in tolterodine (VIII) lower than 0.10% as measured by HPLC.

$^1$H-NMR (300 MHz, $CDCl_3$, 28° C.): δ 7.40-7.15 (m, 5H); 7.05 (dd, 1H); 6.88 (d, 1H); 6.74 (d, 1H); 4.50 (dd, 1H); 4.42 (s, 2H); 3.24 (m, 2H); 2.72 (m, 1H); 2.46-2.28 (m, 2H); 2.10 (m, 1H); 1.10 (dd, 12H).

Example 2

Synthesis of R-(+)-2-(3-diisopropylamino-1-phenyl-propyl)-4-hydroxymethyl-phenyl isobutyric ester (Fesoterodine)

A sodium hydroxide solution (3.30 g, 81.6 mmols) in water (25 ml) and a solution of R-(+)-2-(3-Diisopropylamino-1-phenyl-propyl)-4-hydroxymethyl-phenol of formula (III) prepared as in Example 1 (9.30 g, 27.2 mmols) in toluene (30 ml) are placed in a round-bottom flask under inert atmosphere at room temperature. The reaction mixture is slowly added under strong stirring with an isobutyryl chloride solution (3.50 g, 32.7 mmols) in toluene (20 ml). After completion of the addition, the mixture is left under stirring for a further 10 minutes, the phases are separated and the organic phase is concentrated to a residue. 11.0 g of product are obtained as a pale yellow oil, in 98% yield and with a content in tolterodine (VIII) lower than 0.05% and in a compound of formula (IX) lower than 0.01%.

$^1$H-NMR (300 MHz, CDCl$_3$, 28° C.): δ 7.34 (d, 1H); 7.28-7.12 (m, 6H); 4.62 (s, 2H); 4.12 (t, 1H); 2.98 (m, 2H); 2.80 (m, 1H); 2.34 (m, 2H); 2.14 (m, 2H); 1.32 (dd, 6H); 0.92 (dd, 12H).

Example 3

Synthesis of R-(+)-2-(3-diisopropylamino-1-phenyl-propyl)-cresol isobutyrate (Tolterodine isobutyrate, of Formula IX)

R-(+)-2-(3-Diisopropylamino-1-phenyl-propyl)-cresol (tolterodine of formula VIII) (13.7 g, 42.2 mmols) is dissolved in a sodium hydroxide solution (3.38 g, 84.4 mmols) in water (7 ml) and tetrahydrofuran (130 ml) in a round-bottom flask, under inert atmosphere at room temperature. The reaction mixture is slowly added with isobutyryl chloride (5.85 g, 54.8 mmols) under strong stirring. After completion of the addition, the mixture is left under stirring for 1 hour, then concentrated and the residue is taken up with toluene and water. The phases are separated and the organic one is concentrated under reduced pressure. 16.0 g of product are obtained as a pale yellow oil, in 96% yield and 98% chemical purity as evaluated by HPLC.

Example 4

Synthesis of methyl 3-(3-diisopropylamino-1-phenyl-propyl)-4-hydroxy-benzoate (Compound of Formula II)

Methyl 4-hydroxy-benzoate (52.0 g, 340 mmols) is suspended in methanesulfonic acid (90 ml) in a round-bottom flask under inert atmosphere, and the mixture is heated to a temperature of 50-55° C. 3-Diisopropylamino-1-phenyl-propan-1-ol (20.0 g, 85.0 mmols) is slowly added thereto in about 2 hours and the hot mixture is reacted for 5-6 hours. The mixture is cooled to room temperature and slowly poured into ice/water (200 g) under strong stirring. The product is extracted with dichloromethane (200 ml) and the organic phase is washed with a 10% sodium hydroxide solution (2×100 ml), then with an ammonium chloride aqueous solution to neutral pH. 28.9 g of product are obtained in 92% yield.

$^1$H-NMR (300 MHz, CDCl$_3$, 28° C.): δ 7.74 (dd, 1H); 7.50 (d, 1H); 7.34-7.16 (m, 5H); 6.88 (d, 1H); 4.50 (dd, 1H); 3.76 (s, 3H); 3.26 (m, 2H); 2.74 (m, 1H), 2.40 (m, 2H); 2.16 (m, 1H); 1.10 (dd, 12H).

Example 5

Preparation of the Diastereomeric Salt of a Compound of Formula (II) with (+)-2,3-dibenzoyl-D-tartaric acid Racemic methyl 3-(3-diisopropylamino-1-phenyl-propyl)-4-hydroxy-benzoate (22.0 g, 59.5 mmols) is dissolved in ethanol (320 ml) in a round-bottom flask under inert atmosphere, at a temperature of about 60° C., and (+)-2,3-dibenzoyl-D-tartaric acid (11.1 g, 31.0 mmols) is added thereto. The mixture is left to spontaneously cool for 16-18 hours to room temperature and the suspended solid is filtered, washing with ethanol (3×25 ml). The product is dried in a static dryer at 50° C. under reduced pressure to obtain 20.4 g of product in an R/S enantiomeric ratio of 95:5, as evaluated by chiral HPLC.

$^1$H-NMR (300 MHz, DMSO-d$_6$, 28° C.): δ 7.94 (d, 4H); 7.78 (dd, 1H); 7.64-7.56 (m, 3H); 7.45 (t, 4H); 7.28-7.10 (m, 5H); 6.86 (d, 1H); 5.64 (s, 2H); 4.30 (dd, 1H); 3.75 (s, 3H); 3.40 (m, 2H); 2.75-2.50 (m, 2H); 2.25 (m, 2H); 0.96 (dd, 12H).

Example 6

Preparation of the Diastereomeric Salt of a Compound of Formula (II) with (−)-2,3-Dibenzoyl-L-tartaric acid Racemic methyl 3-(3-diisopropylamino-1-phenyl-propyl)-4-hydroxy-benzoate (22.0 g, 59.5 mmols) is dissolved in ethanol (320 ml) in a round-bottom flask under inert atmosphere at a temperature of about 60° C. and (−)-2,3-dibenzoyl-L-tartaric acid (11.1 g, 31.0 mmols) is added thereto. The mixture is left to spontaneously cool for 16-18 hours to room temperature and the suspended solid is filtered, washing with ethanol (3×25 ml). The product is dried in a static dryer at 50° C. under reduced pressure to obtain 20.4 g of product in an S/R enantiomeric ratio of 95:5, as evaluated by chiral HPLC.

$^1$H-NMR (300 MHz, DMSO-d$_6$, 28° C.): δ 7.94 (d, 4H); 7.78 (dd, 1H); 7.64-7.56 (m, 3H); 7.45 (t, 4H); 7.28-7.10 (m, 5H); 6.86 (d, 1H); 5.64 (s, 2H); 4.30 (dd, 1H); 3.75 (s, 3H); 3.40 (m, 2H); 2.75-2.50 (m, 2H); 2.25 (m, 2H); 0.96 (dd, 12H).

Example 7

Preparation of the Diastereomeric Salt of a Compound of Formula (II) with S-(+)-Camphorsulfonic Acid Racemic methyl 3-(3-diisopropylamino-1-phenyl-propyl)-4-hydroxy-benzoate (15.0 g, 40.6 mmols) is dissolved in ethanol (50 ml) in a round-bottom flask under inert atmosphere at a temperature of about 50° C. and S-(+)-camphorsulfonic acid (9.9 g, 42.6 mmols) is added thereto. The mixture is left to spontaneously cool for 16-18 hours at room temperature and further cooled with an ice bath for 3-4 hours. The suspended solid is filtered and washed with cold ethanol (3×10 ml) and then dried under reduced pressure in a static dryer at a temperature of 50° C. 10.8 g of the salt are obtained in an R/S enantiomeric ratio of 99.8:0.2 as evaluated by chiral HPLC.

Example 8

Synthesis of methyl R-(−)-3-(3-diisopropylamino-1-phenyl-propyl)-4-hydroxy-benzoate (Compound of Formula IIa)

The (+)-2,3-dibenzoyl-D-tartaric acid salt of methyl R-(−)-3-(3-diisopropylamino-1-phenyl-propyl)-4-hydroxy-benzoate (14.5 g, 24.1 mmols) is suspended in a mixture of ethyl acetate (100 ml) and sodium bicarbonate saturated solution (100 ml) in a round-bottom flask under inert atmosphere, with strong stirring until disappearance of the solid. The organic phase is separated and the aqueous phase is extracted with ethyl acetate (2×50 ml). The combined organic phases are concentrated to a residue to obtain the title product.

The invention claimed is:

1. A process for the preparation of a compound of formula (I), or a salt thereof,

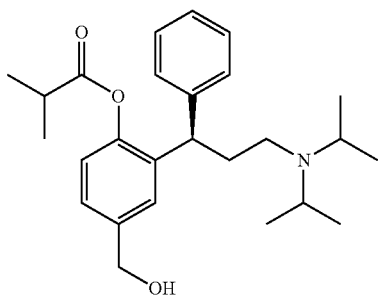
(I)

containing an amount of a compound of formula (VIII)

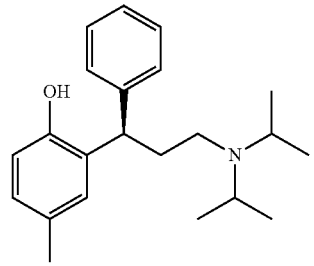
(VIII)

equal to or lower than 0.05% and/or an amount of a compound of formula (IX)

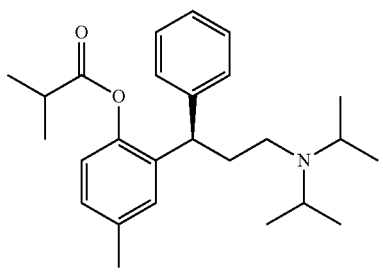
(IX)

equal to or lower than about 0.1%, comprising:
the chemoselective reduction of the carboxylate group of a compound of formula (IIa)

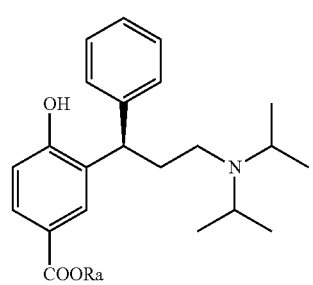
(IIa)

wherein Ra is a $C_1$-$C_6$ alkyl, to obtain a compound of formula (III), and the

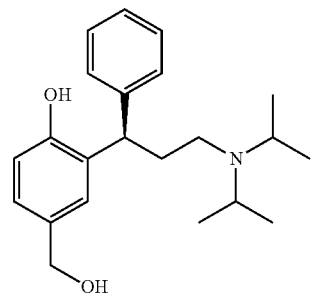
(III)

subsequent selective esterification of the phenolic hydroxy group of the resulting compound of formula (III) to obtain a compound of (I), wherein the chemoselective reduction comprises:
a) the treatment of a compound of formula (IIa), as defined above, with sodium hydroxide or potassium hydroxide in an organic solvent to obtain a phenate intermediate of formula (X)

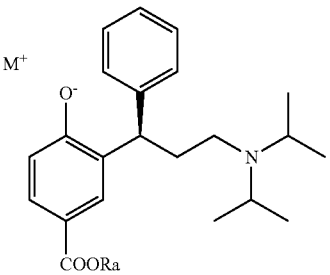
(X)

wherein Ra is as defined above; and $M^+$ is $Na^+$ or $K^+$; and
b) the subsequent reduction with lithium aluminium hydride in an organic solvent.

2. A process according to claim 1, wherein in the treatment of a compound of formula (IIa) with sodium hydroxide or potassium hydroxide an amount of sodium or potassium hydroxide, stoichiometric to the compound of formula (IIa) is used.

3. A process according to claim 1, wherein the treatment of a compound of formula (IIa) with sodium or potassium hydroxide is carried out in a solvent selected from a $C_3$-$C_8$ ketone, a cyclic or acyclic ether, an ester and a $C_1$-$C_6$ straight or branched alkanol.

4. A process according to claim 1 wherein the reduction of the phenate intermediate of formula (X) is carried out in presence of a cyclic ethereal or acyclic ethereal solvent, preferably tetrahydrofuran.

5. A process according to claim 1, wherein the amount of lithium aluminium hydride is at least stoichiometric to the compound of formula (X).

6. A process according to claim 1 for preparing a compound of formula (I) or a salt thereof, further comprising the use of a compound of formula (VIII) and/or (IX), as an analytical standard.

7. A process for the preparation of the (S) enantiomer of a compound of formula (I), as defined in claim 1, or a salt thereof, containing an amount of the (S) enantiomer of a compound of formula (VIII), as defined in claim 1, equal to or lower than 0.05% and/or an amount of the (S) enantiomer of the compound of formula (IX), as defined in claim 1, equal to or lower than about 0.1%, comprising the chemoselective reduction of the carboxylate group of a compound of formula (IIb),

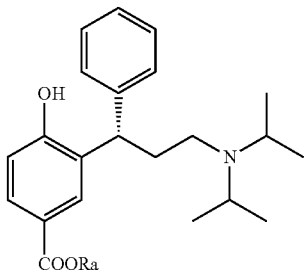

wherein Ra is as defined in claim 1, to obtain the (S) enantiomer of a compound of formula (III), as defined in claim 1, and the subsequent selective esterification of the phenolic hydroxy group of the resulting (S) enantiomer of a compound of formula (III) to obtain the (S) enantiomer of a compound of (I), and wherein the chemoselective reduction is carried out according to steps a) and b) as claimed in claim 1.

8. The process according to claim 1, wherein the amount of a compound of formula (VIII) is equal to or higher than about 0.0001%.

9. The process according to claim 1, wherein the amount of a compound of formula (IX) is equal to or higher than about 0.0001%.

10. The process according to claim 1, further comprising converting a compound of formula (I) into a salt thereof.

11. The process according to claim 5, wherein the amount of lithium aluminium hydride is comprised between about 1 and 5 moles as compared to the moles of the compound of formula (X).

12. The process according to claim 7, wherein the amount of the (S) enantiomer of a compound of formula (VIII), as defined in claim 1, is equal to or higher than about 0.0001% and/or an amount of the (S) enantiomer of the compound of formula (IX), as defined in claim 1, is equal to or higher than about 0.0001%.

13. The process according to claim 7, further comprising converting a compound of formula (I) into a salt thereof.

14. The process according to claim 4, wherein the cyclic ethereal solvent is tetrahydrofuran.

15. The process according to claim 6, wherein the salt of the compound of formula (I) is a fumarate, citrate, hydrochloride, or sulphate salt.

* * * * *